United States Patent [19]

Spinello

[11] Patent Number: 5,180,371
[45] Date of Patent: Jan. 19, 1993

[54] HYPODERMIC ANESTHETIC INJECTION APPARATUS AND METHOD

[75] Inventor: Ronald P. Spinello, Westbury, N.Y.

[73] Assignee: Spintech, Inc., York, Pa.

[21] Appl. No.: 652,495

[22] Filed: Feb. 8, 1991

Related U.S. Application Data

[63] Continuation of Ser. No. 191,138, May 16, 1988, abandoned, which is a continuation-in-part of Ser. No. 868,745, May 30, 1986, Pat. No. 4,747,824.

[51] Int. Cl.⁵ .......................................... A61M 31/00
[52] U.S. Cl. .................................... 604/118; 604/51; 604/207
[58] Field of Search ............... 604/131, 152, 154, 155, 604/156, 118, 905, 229, 207, 228, 51, 20; 128/DIG. 1, 665; 433/84, 85, 89, 90, 112

[56] References Cited

U.S. PATENT DOCUMENTS

| | | | |
|---|---|---|---|
| 3,395,704 | 8/1968 | Frey et al. | 604/154 |
| 3,650,093 | 3/1972 | Rosenberg | 604/152 |
| 3,720,211 | 3/1973 | Kyrias | 604/155 |
| 3,971,375 | 7/1976 | Hill | 604/207 |
| 4,141,359 | 2/1979 | Jacobsen et al. | 604/20 |
| 4,168,707 | 9/1979 | Douvas et al. | 604/118 |
| 4,261,360 | 4/1981 | Perez | 604/118 |
| 4,323,066 | 4/1982 | Bourdon | 604/228 |
| 4,392,847 | 7/1983 | Whitney et al. | 604/118 |
| 4,430,079 | 2/1984 | Thill et al. | 604/154 |
| 4,465,474 | 8/1984 | Mardorf et al. | 604/154 |
| 4,508,532 | 4/1985 | Drews et al. | 604/155 |
| 4,581,022 | 4/1986 | Leonard | 604/229 |
| 4,613,328 | 9/1986 | Boyd | 604/900 |
| 4,767,406 | 4/1988 | Wadham et al. | 604/155 |

Primary Examiner—Paul J. Hirsch
Attorney, Agent, or Firm—Hoffmann & Baron

[57] ABSTRACT

An aspirating hypodermic syringe and method for injecting dental anesthetic in which anesthetic flow through the needle is established independently of the fingers of the operator and in which different rates of flow are provided, including positive flow while the needle is entering the tissue. Effective aspiration in syringes which use expendable anesthetic vials is assured by means of a yieldable resistance member in the syringe which holds the vial with sufficient force to enable the syringe plunger to lock positively onto the piston of the vial.

7 Claims, 7 Drawing Sheets

HYPODERMIC ANESTHETIC INJECTION APPARATUS AND METHOD

This is a continuation of copending application Ser. No. 07/191,138 filed on May 16, 1988 now abandoned, which is a continuation-in-part of application Ser. No. 868,745 filed May 30, 1986 now U.S. Pat. No. 4,747,824.

This invention relates to aspirating hypodermic syringe apparatus and methods, particularly as applied to dentistry, for injecting anesthetic safely and painlessly.

BACKGROUND OF THE INVENTION

Almost 100 years ago the excruciating pain of dental extraction, drilling and reconstruction was eliminated by the invention of local anesthetics. Ever since, however, one smaller but often agonizing pain has remained; ironically, it is the pain of the hypodermic injection itself. All practical attempts to eliminate it have failed.

While narrow gauge, sharp hypodermic needles can be inserted into the soft fleshy tissues of say an upper arm essentially without pain, save possible psychological pain, the pain of a hollow needle inserted into the hard, relatively inelastic gum and mouth tissues to engage the bone which carries the nerves to the teeth, is more often than not real. It is also complex. Pain can be felt when the needle first punctures the firm tissue and thereafter as the needle tip cuts through the tissue. Not infrequently the pain is amplified as the moving needle cuts out a tiny core of tissue which enters the bore in the hollow needle. Pain can be felt if the needle scrapes the bone membrane and even greater pain can be felt if the injected liquid mass distends and tears the tissue, particularly the interior tissue, away from the bone in one of the most sensitive portions of the body, before absorption and numbing occur. And pain can be felt if either the dentist or the patient or both are not steady, causing traumatic lateral displacement of the embedded needle.

The present state of the art in hypodermic anesthetic injections, particularly dental injections, is at best a hit or miss art reflecting the skill and luck of the operator rather than being a scientifically repeatable procedure. The tools are clumsy and ill-suited to their task, making the administration of local anesthetics in dentistry one of the less pleasant procedures for both the dentist and the patient alike.

The present invention has for its object to eliminate pain in all phases of and for all types of hypodermic anesthetic injection including four in dentistry considered most difficult and painful: the palatal, the mandibular, the interligamentary, and the maxillary anterior.

Another object of the invention is to provide a factory-sterilized, assembled and sealed hypodermic syringe sub-assembly to provide an unbroken chain of sterility from manufacturer to patient.

Another object of the invention is to provide a universal hypodermic syringe which can be used for all known dental injection procedures, which is pleasant and easy to use and which affords the dentist extraordinarily acute tactile response characteristics essential to good dentistry.

Another object of the invention is to provide a local anesthetic injection apparatus and method which reduces the amount of anesthetic required to perform dental procedures.

Still another object of the invention is to provide an aspirating hypodermic syringe using expendable pre-filled vials in which the reliability of the aspirating test cycle is assured.

BRIEF DESCRIPTION OF THE INVENTION

Nerves exit from the brain as large bundles or trunks. Much like a tree, the major nerves branch into smaller bundles. This branching continues until finally the nerves become individual fibers and spread in and around the cells of most all tissues in the body. On a microscopic level each nerve fiber is composed of cells aligned end on end and interconnected at each end by a synapse. When a stimulus is applied to a nerve ending, an electrical impulse or signal is transmitted from nerve cell to nerve cell and regenerated across each synapse, until it reaches the brain, where it is interpreted, for example, as cold or hot and, when in the extreme, pain. When a local anesthetic solution is applied to a nerve, it blocks the signal transmission. The brain therefore receives no sensory information from the part affected by the anesthetic. It is believed that it occurs when the anesthetic comes in contact with a nerve part, rendering it instantly inoperative.

It is the object of dental injections to render the nerve bundles which supply the teeth and supporting structures free of pain sensation. These nerve bundles pass from the brain through the jaw bone to the teeth and gums. In instances in which the bone is spongy such as in the upper jaw (maxilla) the anesthetic can be placed at the outside bone surface adjacent to the tooth. The solution is absorbed by the porous bone and infiltrates to the tooth nerve. In other instances where the jaw bone is dense as it is in the lower jaw (mandible), the dentist must either block the nerve before it enters the jaw or he may attempt to force the anesthetic into the ligament space between the tooth root and the bone.

In all cases there is a delay before the anesthetic solution penetrates through the various tissues, and until it disables all of the fibers in the nerve bundle. During the injection procedure the needle point severs through tissues which contain live nerve endings, the hollow tip of the needle can cut a core of tissue which enters the leading end of the needle, the injected anesthetic solution can stretch and tear the tissue, and the needle can by mistake be moved laterally through the tissue, all causing their respective components of pain before the nerves in the main trunk are blocked.

The present invention provides a means whereby the nerves are disabled in the area of the injection and in the path of the needle before pain sensation is perceived. The needle is held in a stablilized trajectory and advanced slowly at a rate preferably, for example, not to exceed 6 mm/sec. through the tissues, and a flow of anesthetic solution is established concomitantly at a constant slow rate not to exceed 0.25 to 1.0 cc. per minute, surrounding the moving needle with a sheathing of anesthetic solution. At the same time, by virtue of the sustained positive pressure in the needle barrel, a core of tissue is not cut out by the moving needle. Since nerve disability is instantaneous, needle penetration is not perceived as pain. When the needle reaches bone, if the constant and painless rate of flow of anesthetic is continued, tissue numbness occurs prior to tissue stretching. Once the surrounding tissues have been rendered numb, the rate of flow can be increased to expedite the painless procedure.

The instrument in accordance with one preferred embodiment of the invention, includes a low-inertia needle and elongated handle assembly either connected by a flexible conduit to an anesthetic vial, or itself containing an anesthetic vial, all of which can be pre-sterilized and disposable; stabilizing means for referencing needle movement and position to the site; and an activator or pump to at least preclude back flow or expel extremely small volumes of anesthetic at a controlled rate, and, selectively, relatively larger volumes at high flow rates.

The needle assembly can comprise a narrow pencil-grip handle to allow the thumb and forefinger of the operator to implant the needle delicately to sense the essential proximity to bone while the other fingers stabilize the needle assembly against a fixed reference such as the teeth. In the case of the mandibular injection which is deep in the sides of the mouth at the ascending ramus of the lower jaw bone and which seeks a small window in the bone to the large bundle of interior nerves serving all lower teeth, the handle can be stabilized to the lower jaw, either by the fingers of the dentist or by a bite block, thus relieving the dentist of the fatigue attendant a large volume (about 2 cc.) injection over a period of up to one minute. The needle can be moved axially for a controllable distance and direction without the loss of sensitivity by the fingers holding the unit. If desired, a movable pressure pad and needle guiding and shielding tip can be used to pre-engage the injection site as the needle is moved through it into the tissue, or it can be manually moved to expose only as much of the needle as is required for the injection.

The maintenance of positive pressure in the needle for preventing reverse flow or, preferably, for expressing extremely small amounts of the liquid anesthetic from the needle tip are critical at the outset of the injection. It is difficult if not impossible to hold pressure or to achieve consistently low flow rates using a conventional thumb-actuated syringe, particularly while the needle tip, invisible to the dentist, is cutting through the tissue. In accordance with the invention, an initial flow rate not in excess of 0.25 to 1.0 cc. per minute or approximately 0.5 to 1.5 drops per second (from a 30 gauge needle) is generated beginning not later than the outset of the initial needle penetration. This can be best achieved by separating the liquid pumping function from the hand which performs the needle implant. A foot-controlled motor is one preferred embodiment in which the pumping action is of variable speed or rate and in which the anesthetic pumping action is bidirectional to achieve the essential test to determine that the needle is not implanted in a vein or artery when the high injection rate begins. The pumping action can be arranged so that the pressure of the anesthetic is reduced below the patient's blood pressure for a controlled interval, briefly and automatically for one or more times during each injection and in any event at the instant before high volume pumping begins in a fixed spot. This allows blood to back-flow into a viewing area in the syringe in the event the tip is implanted by error in a vein or artery.

In one preferred embodiment of the invention in which the hypodermic syringe uses pre-filled expendable vials of anesthetic and containing their own piston, push-pull driving engagement of the actuator of the syringe with the piston is made error-free by providing a yieldable resistance force on the vial which exceeds the force required to fully engage the actuator with the piston in its essential push-pull coupling.

BRIEF DESCRIPTION OF THE PRIOR ART

The sources of pain in hypodermic injections have long been recognized. Dental schools for example, teach care and steadiness in implanting the needle at precise locations, the need to achieve reverse flow to prevent injection of anesthetic directly into a vein, and an undefined slow injection rate, at least at first until numbness is achieved. The classic syringe instrument for doing all of this, a direct derivation from the medical intramuscular, subcutaneous and intravenous syringes, puts a heavy essentially unachievable burden on the dentist if the procedure is to be painless. The instrument is too heavy and it is held incorrectly to reflect optimum tactile sensations between the needle and the fingers of the dentist. It is all but impossible to achieve the uniformly low flow rates called for by the present invention.

U.S. Pat. No. 1,046,166 suggests separating the anesthetic pumping and needle implanting functions by using the foot to pump the liquid. It achieves pressures beyond those achievable by the thumb "to force the liquid into the tooth dentin", but is not concerned with low inertia, low precision-controlled flow rates and the combination of needle insertion and preliminary expression of anesthetic. U.S. Pat. No. 3,496,937 recognizes the advantage of a pencil grip and of at least partially freeing the thumb from the axial-thrust pumping action but at the expense of increased size and weight, and it lacks any way of achieving a back-flow or aspiration cycle to test for the unintended and dangerous insertion of the needle directly into a vein or artery rather than the local tissue. Also, the stored energy in the resilient (or elastomeric) container is such that maximum pressure and flow occur at the outset and decrease with time, which is the opposite of that which is required in accordance with the present invention. U.S. Pat. No. 966,128 discloses a power syringe adapted to be connected by a flexible rotating shaft to a dental lathe so that the dentist is freed from delivering the pumping forces. It does not disclose the method or apparatus whereby low, precision-controlled flow rates are established concomitantly with needle penetration, nor are selective high and low expression rates suggested. Overall, the prior art does not teach the combination of structures or the method which renders hypodermic anesthetic procedures repeatably painless, safe and efficient for all types of injections.

DESCRIPTION OF PREFERRED EMBODIMENTS

Figure 1A:
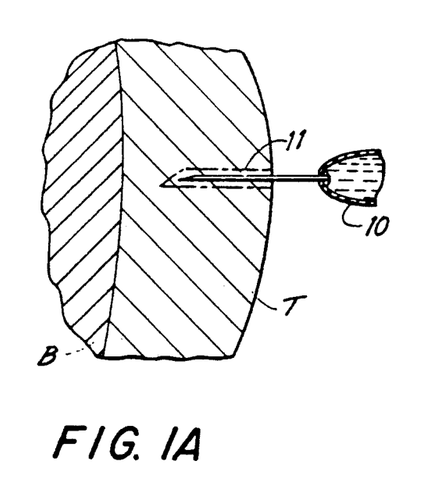
FIGS. 1A and 1B are diagrammatic representations in enlarged scale and in cross section illustrating the method of the invention as applied to one form of dental anesthesia.
Figure 1B:
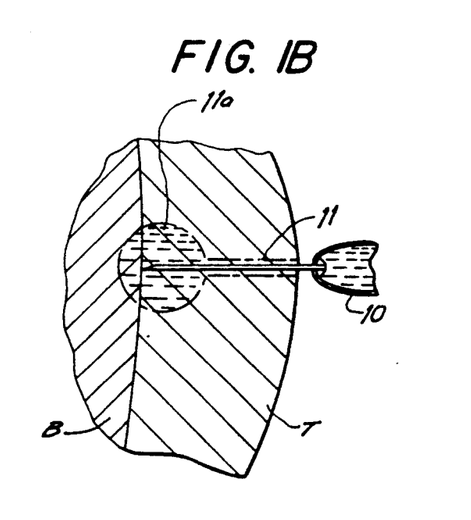
Figure 2A:
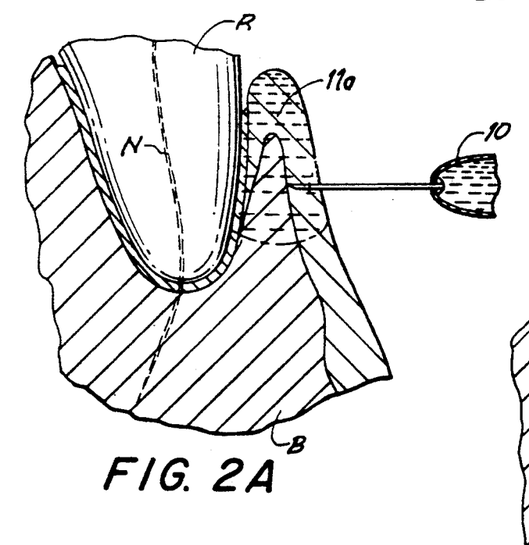
FIGS. 2A and 2B are diagrammatic representations in enlarged scale and in cross section illustrating the method of the invention as applied to an interligamentary dental anesthetic injection.
Figure 2B:
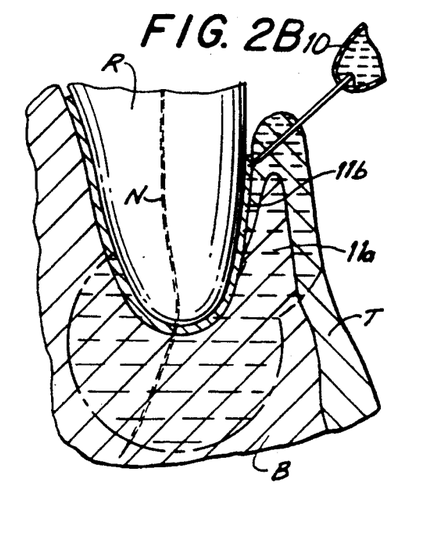
Figure 3:
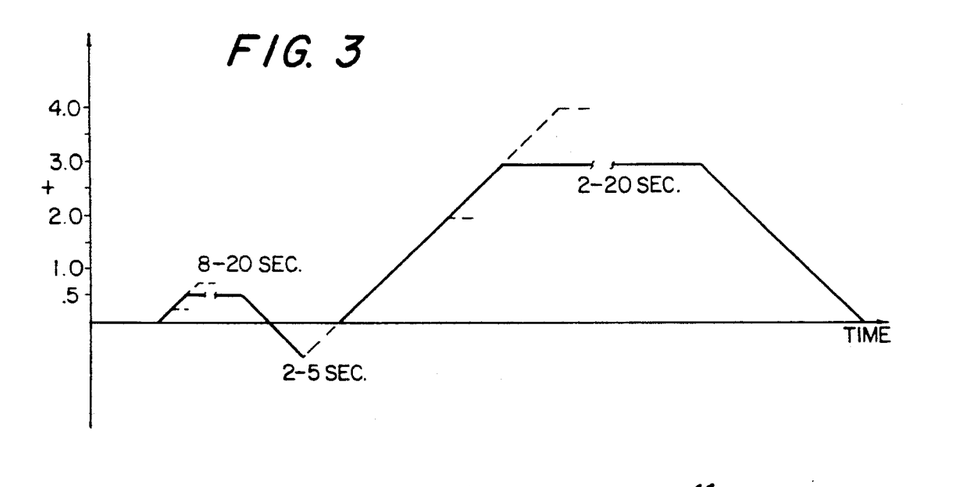
FIG. 3 is an anesthetic flow rate vs. time graph showing representative values for carrying out the invention.

The method of the present invention is described having reference to FIGS. 1 through 3. In FIGS. 1A and 1B the hollow pointed needle of a hypodermic syringe 10 is shown penetrating the soft gingival tissue T covering the bone B in which the root of a tooth (not shown) is imbedded. Prior to insertion of the needle into the tissue the syringe, filled with liquid anesthetic is actuated to the point at which a small drop appears at the opening tip of the needle. A flow rate for the anesthetic is then established through the needle not to exceed 0.25 to 1.0 cc. per minute by means of apparatus described below. As the needle pierces the tissue preferably at a rate of penetration not exceeding 6 mm. per second, anesthetic is expressed continuously from the needle resulting in a sheath 11 of anesthetic from in front of the tip rearward which anesthetizes the path of travel of the needle rendering the insertion painless. When the needle reaches its desired position adjacent the bone, the relatively low continuous rate of anesthetic expression is continued creating a plume 11a constituting an expanded zone of tissue which is anesthetized due to infiltration of anesthetic into the soft tissue and the bone. This portion of the injection is termed "intermediate".

Referring to FIG. 3, this initial period of relatively low level anesthetic expression rate constituting the intermediate injection is shown on the time-rate graph as taking between 8 and 20 seconds, depending on the injection site and the particular requirements of the patient.

After the initial period of 8 to 20 seconds of low-rate injection of anesthetic the surrounding area becomes sufficiently anesthetized to enable the operator to increase the rate of flow to 2 to 4 cc. per minute until the desired degree of numbing is achieved. Such high rates of anesthetic expression normally cause pain due to stretching and tearing of the tissues, but having been pre-anesthetized no sensation is felt. Prior to beginning the high rate of injection a negative pressure relative to veinal blood pressure of the patient is established at the needle tip to reverse the fluid flow back into the syringe where it can be viewed by the operator for the presence of blood indicating a vein or artery has been entered which requires that the needle be repositioned. As shown in FIG. 3, the timing for the negative pressure phase can be on the order of 2 to 5 seconds. The actual reverse flow or aspiration of fluid represents the small total volume needed to fill the needle and viewing area beyond.

The high speed expression of anesthetic, if needed, can be for a duration of 2 to 20 seconds depending on the nature of the injection. A mandibular injection at the ascending ramus of the lower jaw, for example, usually requires a full 2 cc. injection in a site deep within the lower jaw and takes the maximum time. The elapsed time of course varies with the rate of flow the upper limit of which is determined by the ability of the site to absorb the anesthetic liquid without creating such a large volume of unabsorbed liquid at the needle tip that tissue is torn from the bone.

Referring to FIGS. 2A and 2B, in which like parts are identified by like reference characters, there is illustrated an injection known as interligamentary, a normally difficult and painful injection in which anesthetic is forced under high pressure through the ligament space 11b between the bone and the roots of the tooth to the nerve N which enters the tooth at the root tip. The injection site is prepared by an intermediate injection using the low continuous flow rate of between 0.25 and 1 cc. per minute as the needle is inserted and thereafter against the bone for a total of 8 to 20 seconds (FIG. 2A) to achieve preliminary numbing. The needle is then placed as shown in FIG. 2B and, after aspiration a brief high speed injection rate of 2 to 4 cc. per minute is established to drive the anesthetic to the nerve N via the periodontal ligament space 11b. This enables the dentist to anesthetize an individual tooth for treatment with a minimum amount of anesthetic. The apparatus described below provides the flow rate and pressure necessary to achieve this injection method.

Figure 4:
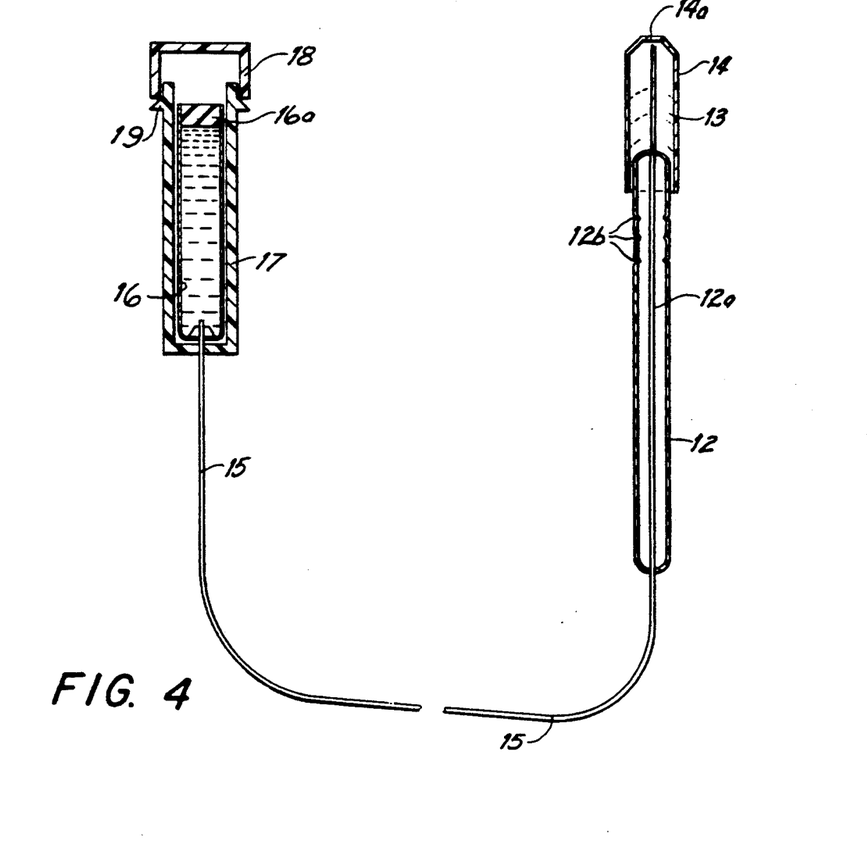
FIG. 4 is a drawing partly in cross section illustrating an expendable, sterile, pre-charged anesthetic and syringe kit in accordance with the invention.
Figure 5:
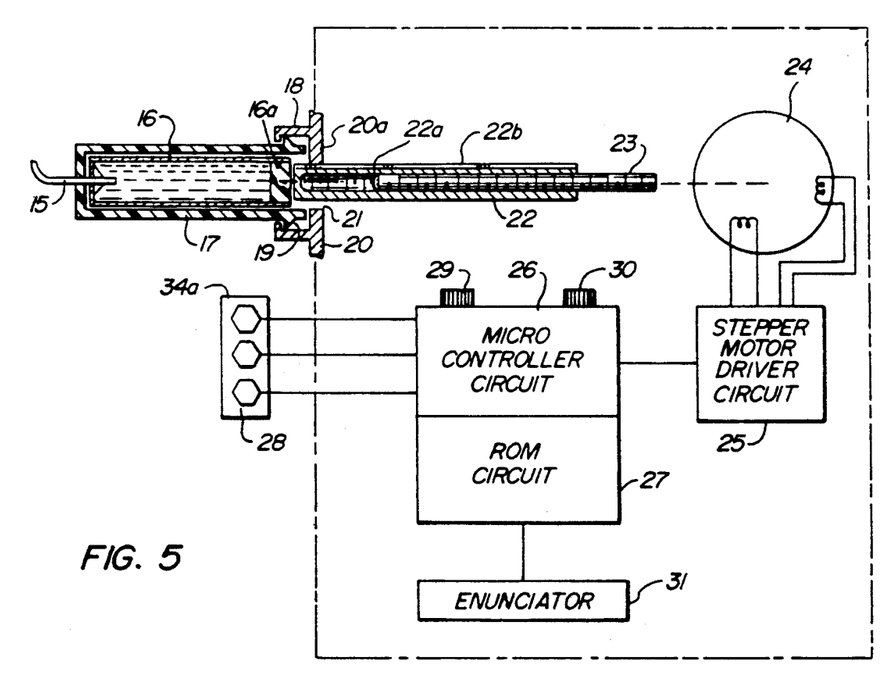
FIG. 5 is a schematic diagram partly in cross section illustrating one form of apparatus in accordance with the invention.
Figure 6:
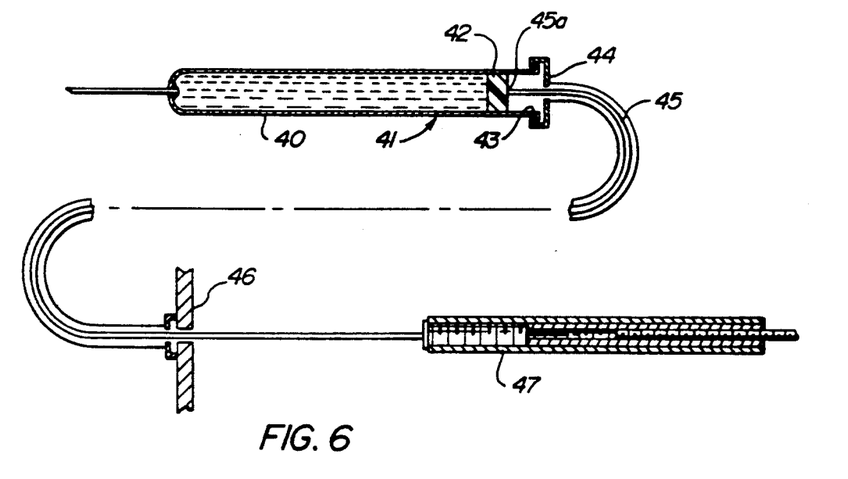
FIG. 6 is a schematic diagram illustrating another embodiment of the invention.

Referring to FIG. 4, there is illustrated an assembly of expendable parts comprising a sterile kit for one injection of anesthetic and used in conjunction with apparatus disclosed in FIGS. 5 and 6. The kit includes a handle or handpiece 12 carrying at one end a hollow hypodermic needle 13, preferably in range of 22 to 30 gauge, within a retractable transparent sheath 14 and connected at the other end to a length of flexible tubing 15 which is highly resistant to collapsing and to stretching. The handpiece 12 can be made of transparent plastic with a central bore 12a and is preferably in the range 8 to 18 cc. in length and 20 to 50 mm. in circumference.

The distal end of the tubing is connected to an anesthetic vial which can be of conventional design formed of glass and containing a movable rubber piston 16a to seal in its 2 cc. anesthetic charge. The vial is housed in a transparent plastic container 17 sealed by removable cap 18. The container includes a resilient rib 19 by means of which it can be mounted in the pumping apparatus of FIG. 5 or 6 as described below.

The initial charge of anesthetic can if desired fill the tubing 15, the handpiece through-bore 12a and the hollow needle 14. With the sheath 14 and cap 18 in place the entire assembly can be factory-sterilized and sealed in a pouch for opening in the presence of the patient and discarded after one use. The sheath 14 includes a pierceable membrane 14a at its outer end so that it can be slid down the handpiece to expose three differing lengths of the needle in which position 1 constitutes an optimum length for an interligamentary injection, position 2 a maxillary injection and position 3 a mandibular injection. If desired indicia 12b can be formed on the handpiece 12 to indicate the three different positions in which the needle is stabilized to different degrees by the pierceable membrane.

Referring to FIG. 5 there is illustrated pumping apparatus for receiving the vial portion 16 of the assembly of FIG. 4 at a point remote from the patient but reachable by the flexible tubing 15. The plastic protective container 17 for the glass vial 16 is mounted in a yieldable coupling 18 so that the rib 19 secures the container and vial against axial movement with respect to a support 20. The support 20, which is part of a motor and motor controller housing (not shown), has an opening 21 through which passes a tubular piston rod 22, the outer end of which engages the rubber piston 16a in vial 16. A conventional barbed tip 22a on the end of the piston enters the rubber piston to enable the piston to be withdrawn slightly when aspiration is called for. The piston rod is internally threaded to receive a drive screw 23 coupled to a reversible stepper motor 24. The piston rod 22 is axially slidably mounted in the support wall 20 and is constrained against rotation by a key 20a on the support and received in a slot or key-way 22b so that it is driven in and out upon activation of the stepper motor 24 to pump or aspirate depending upon the direction of rotation of the drive screw.

The stepper motor 24 is operated by a driver 25 controlled by a micro controller circuit 26 coupled to an ROM circuit 27 programmed to monitor the pulses to the stepper motor to establish limit stops for piston rod positions in and out. The circuit is also programmed to initiate an aspiration cycle, i.e., a small reverse motion for the piston 16a before every "fast" flow rate cycle. The fast, slow and reverse motions of the piston are controlled by the operator for slow, fast and reverse by means of switches 28 preferably foot-controlled or a combination of foot and manual control. The fast flow rate is geared to express liquid anesthetic from the needle tip at a rate of between 2 and 4 cc. per minute and the slow flow at 0.25 to 1.0 cc. per minute. The aspiration cycle is set to achieve gentle reverse motion of the piston on the order of 1 to 2 mm. (or at least sufficient to draw back into the needle and the viewing portion of the handpiece viewable liquid drawn back from the tip of the needle to assure the operator that the needle has not been threaded into an artery or vein). This test must be done before the high rate of expression of anesthetic is commenced, whether it be immediately after the placement of needle in its final position or immediately before the high rate of expression is started. It must be gentle to avoid drawing the vein or artery wall against the opening in the needle.

The micro controller circuit includes manual push switches 29 and 30 for, respectively, manually effecting rapid reverse of the piston rod for reloading and rapid forward for purging the system of air. An enunciator circuit for emitting a small audible tone upon the injection of each, say, 0.5 cc. of anesthetic (measured by clocking the corresponding number of rotations of the shaft 23) provides a means of monitoring the injection without requiring the operator to look away from the site.

It will be understood that the apparatus of FIG. 5 is diagrammatic and can take various forms and arrangements. Reduction gearing can be provided between the motor 24 and shaft 23 if required to maintain constant discharge pressures which are particularly essential for the interligamentary injection requiring high pressure as well as a substantial flow rate to drive the anesthetic through the tooth ligament to the nerve at the root tip. Also, the threaded shaft 23 can be mounted to drive a threaded block follower carrying the piston rod in a laterally offset position relative to the threaded shaft and carried in its independent slide bearings.

In the arrangement of FIG. 6 the anesthetic vial and reservoir 40 are incorporated in the handpiece 41 together with a piston 42 and a coupling rib 43 adapted to be coupled to a drive rod head 44. A sheathed flexible drive rod 45 enters the head 44 and couples through a barbed tip 45a to the piston 42. The other end of the sheathed drive rod is connected to a motor housing 46, with the sheath being secured to the housing and the flexible push-pull drive rod being secured to a reciprocatable drive shaft 47 corresponding to the drive shaft 34 of FIG. 5. The switch controls and motor can also correspond to those of the system of FIG. 5.

Figure 7A:
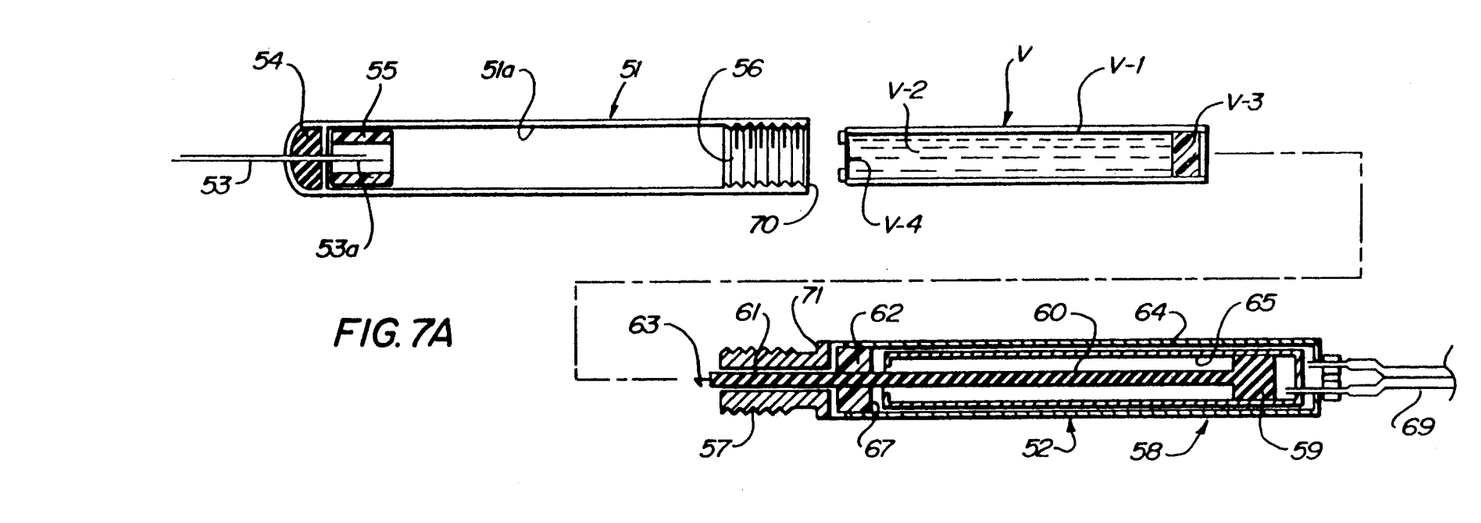
FIG. 7A is an exploded view in longitudinal cross section of a three piece aspirating hypodermic syringe including a needle-carrying portion, a vial of anesthetic solution and an actuating rear portion.
Figure 7B:
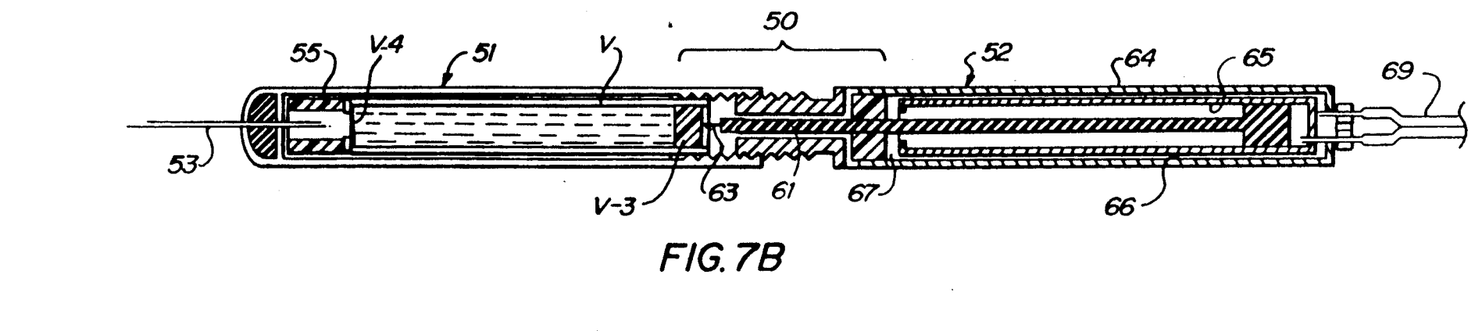
FIG. 7B shows the initial insertion of the anesthetic vial into the front portion.
Figure 7C:
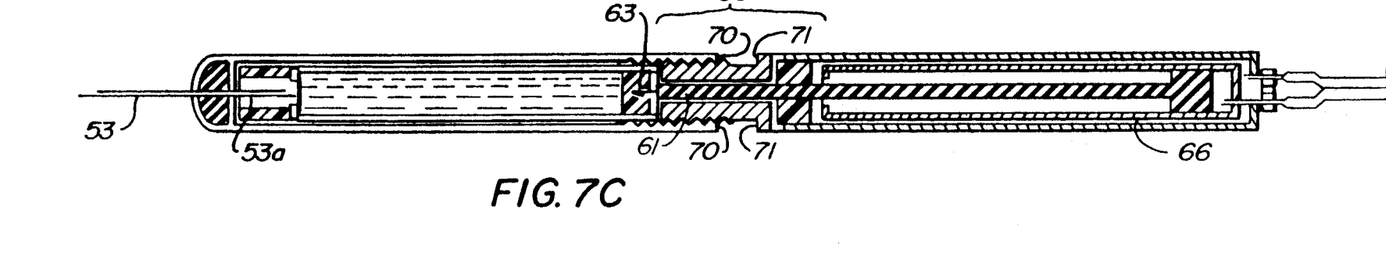
FIG. 7C shows the first stage of mating the front and rear portions of the syringe in which the plunger of the actuator is engaged with the piston in the anesthetic vial.
Figures 7D, 7E, 7F:
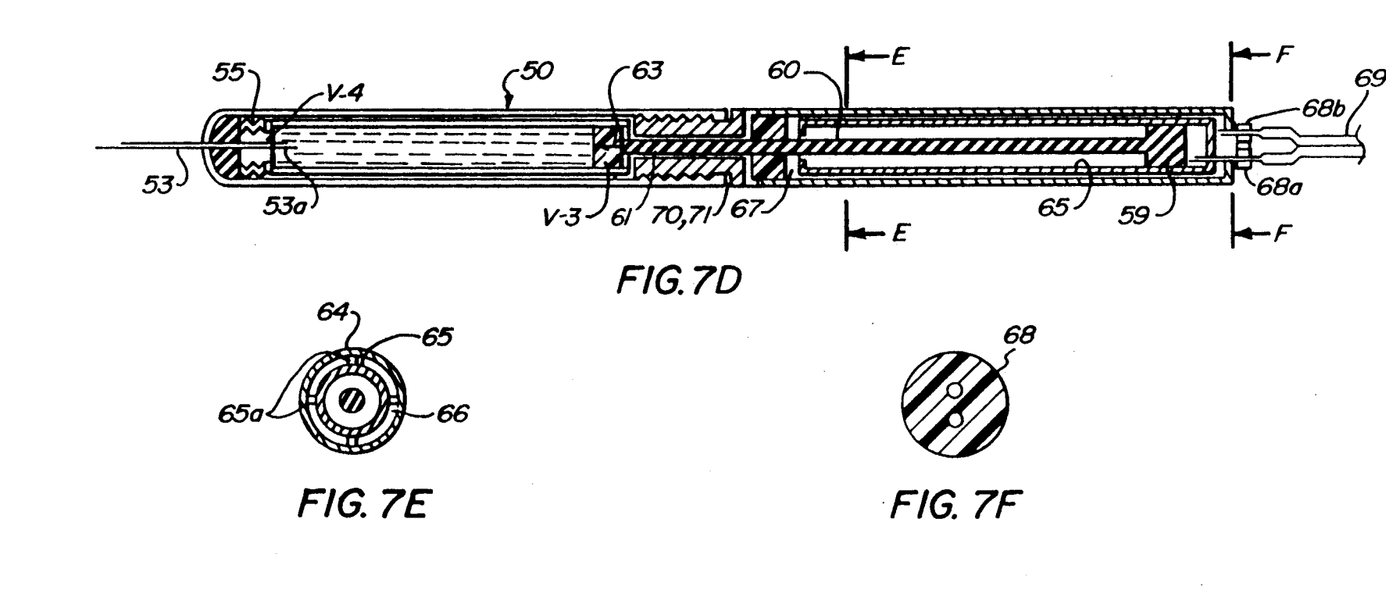
FIG. 7D shows the completed assembly of the hypodermic syringe in which the forward end of the anesthetic vial is engaged with the hollow needle.
FIG. 7E is a view in cross-section taken the line E—E of FIG. 7D looking in the direction of the arrows.
FIG. 7F is a view in cross-section of the hypodermic syringe assembly looking in the direction of the arrows F—F.
Figure 8:
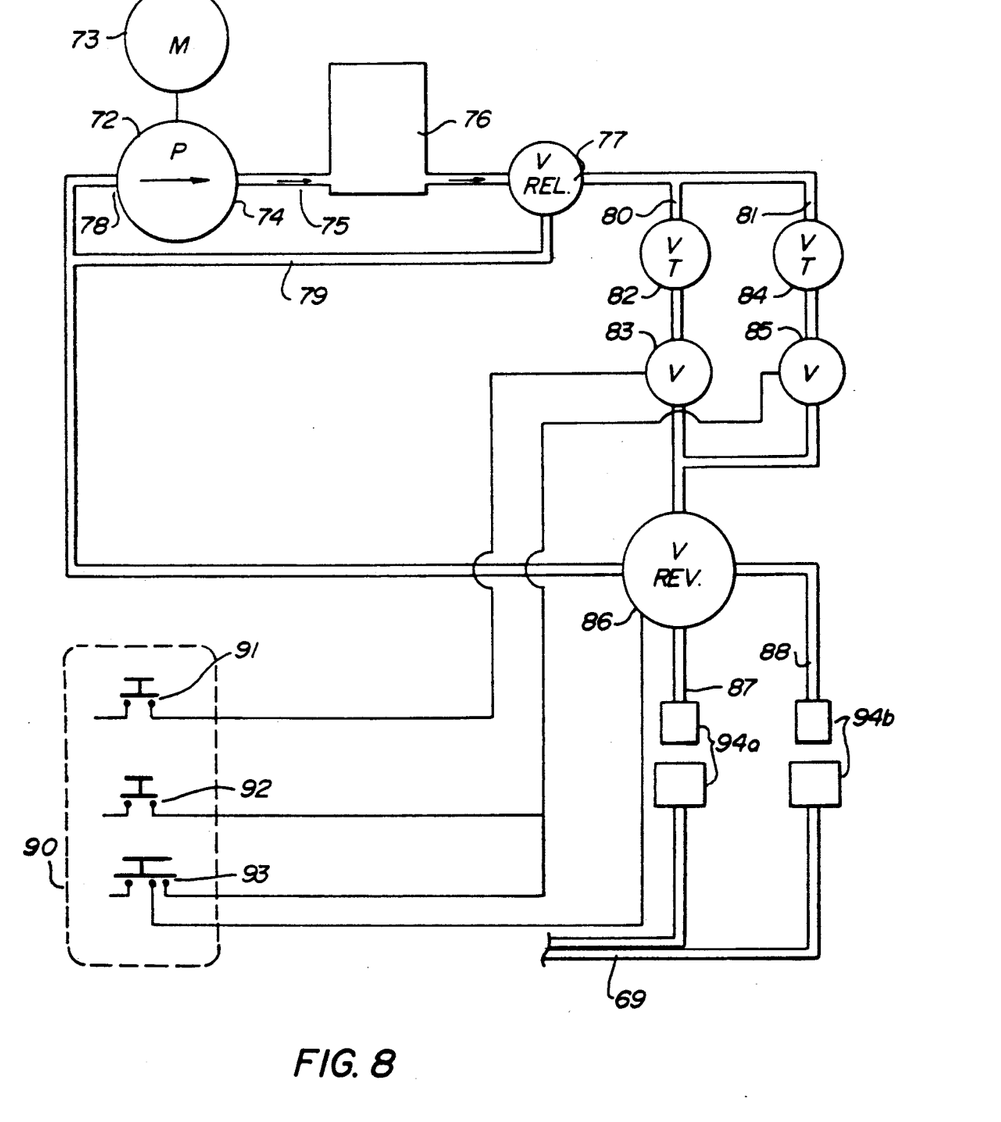
FIG. 8 is a schematic diagram of a hydraulic system particularly adapted to operate a hypodermic syringe of FIGS. 7A-7F from a remote point.

Referring to FIGS. 7A-7F there is illustrated a hypodermic syringe assembly formed in accordance with the present invention and particularly adapted to be actuated from a remote hydraulic power source, an example of which is shown in FIG. 8. The assembled syringe is shown in FIG. 7D and identified by the reference numeral 50. As in the embodiment of FIG. 4 it is designed for finger manipulation like a pencil and preferably has a form factor in which the length is in the range of 8 to 18 cc. with a circumference of 20 to 50 mm. In its preferred embodiment it has a uniform diameter or circumference throughout its entire length.

As best seen in FIG. 7A, hypodermic assembly 50 is comprised of three parts: a front needle-carrying section 51, an anesthetic vial V which can be of conventional design, and an actuating section 52. The front section 51 carries the hollow needle 53 at its forward end mounted in a support bushing 54 coaxially mounted with respect to the cylindrical barrel 51a. The needle mounting is such that the rearward portion 53a of the needle extends into the cylindrical barrel 51a of the front section 51. The needle 53 is sharpened at both ends. A yieldable resistance in the form of a resilient sleeve member 55 is fitted in the forward end of the cylindrical barrel 51 to bear against the bushing 54 and extending rearward into the barrel for a distance exceeding the length of the inner end 53a of the needle 53. The trailing end of the cylindrical barrel can be formed with internal threads 56 for coupling to the actuating section 52.

The anesthetic vial V includes a cylindrical glass body portion V-1 filled with an anesthetic solution V-2 held between a resilient piston V-3 at the rearward end and a pierceable diaphragm V-4 at its forward end. Such vials are conventional in the dental profession.

The actuating section 52 of the syringe includes a forward, externally threaded portion 57 adapted to be threaded into the internally threaded front section 51, and a double-walled cylindrical body portion 58 containing a piston 59 having a forwardly extending piston rod 60 slidably mounted in a guide 61 having a sealing bushing 62. The forward end of the piston rod 60 carries a penetrating hook 63 which is adapted to pierce the piston V-3 in the anesthetic vial V to form a push-pull coupling as is conventional in the art. Not conventional in the art are means to insure that the push-pull coupling is automatically affected.

As best seen in FIG. 7E the cylindrical actuating portion 52 includes an outer cylindrical wall 64, and radially inwardly spaced therefrom, by spacers 65a, an internal cylindrical member 65 containing the piston 59. The space 66 between the concentric cylinders 64 and 65 defines a hydraulic flow path to the forward side of the piston through the space 67 defined by the shortened forward end of the inner cylinder 65. A two-port hydraulic fitting 68 is disposed at the back end of the syringe with its first port 68a connecting to the inner cylinder 65 on the back side of the piston 59 and the second port 68b connecting to front side of the piston 59 through the space 66 between the cylinders 64 and 65 and the space 67. A two-line flexible conduit 69 has its respective lines connected to the ports 68a and 68b at one end and to the power system of FIG. 8 at the other end.

Assembly of the syringe is begun by inserting the vial V into the forward syringe portion 51 until it engages the resilient member 55 as best seen in FIG. 7B. The resilient member 55 prevents the trailing end of the needle 53 from penetrating the forward membrane V-4 in the vial V. The rear actuating portion 52 is then threaded into the forward section 51 to an intermediate point as shown in FIG. 7C, at which time the barb 63 engages and pierces the piston V-3 of the vial V. The strength of the resilient sleeve 55 is selected to exceed the force required for the barb 63 to pierce the piston V-3 thus capturing the piston in a push-pull coupling between the actuating piston 59 and the vial piston V-3. The coupling between the forward and rearward sections 51 and 52 of the hypodermic syringe is then completed until engagement is established between the trailing end 70 of the forward portion 51 and a shoulder 71 formed rearwardly of the threads 57 near the leading end of the rearward portion 52. As best seen in FIG. 7D this action compresses the resilient sleeve 55 which allows the rearward end of the needle 53 to pierce the membrane V-4 in the vial V to provide for anesthetic liquid flow through the hollow needle.

The hydraulic power source as best seen in FIG. 8, includes a power source or motor 73 which can be an electric motor, a pneumatic motor which can have a direct diaphragm coupling to the pump 72, or a hydraulic drive using tap pressure, as is well known in the art. The output 74 of the pump 72 is connected by a conduit 75 containing an accumulator and reservoir 76 connected thereto. A pressure release or modulator valve 77 is connected back to the input 78 of the pump via a conduit 79. The valve 77 is preferably set to maintain a desired constant hydraulic pressure in the system. The conduit 75 is connected to two parallel branch circuits 80 and 81 representing respectively high and low flow rate circuits. The low flow rate circuit 80 includes a throttling valve 82 preset to determine the desired ultimate flow rate from the syringe needle and an on-off control valve 83. Similarly, the high flow circuit 81 includes a throttling valve 84 and a control valve 85. Both circuits are connected to a hydraulic reversing and selector valve 86 the output of which is connected by conduits 87 and 88 to the hydraulic syringe assembly of FIG. 7 via the double conduit 69. Also connected to the reversing valve 86 is a return conduit 89 to the input 78 of the pump 72. A foot control switch 90 having a low-volume forward switch 91, a high-volume forward switch 92 and reverse switch 93 (all of which can be of conventional design) is connected to the control valves 83 and 85 and to the reversing valve 86. Quick connect and disconnect couplings 94a and 94b are provided in respective conduits 87 and 88 and function to maintain pressure and prevent leakage when disconnected.

In operation, the hydraulic system is first fully charged from the power source to the syringe with hydraulic liquid such as silicone oil. In a typical dental procedure, in accordance with the invention, the foot switch is first actuated to establish the desired low flow rate through the needle 53 of the hydraulic syringe at which time the needle is inserted into the patient. The foot switch is then actuated when the needle is implanted to reverse the flow so that the piston 59 and therefore the piston V-3 are pulled back to aspirate fluid from the patient to determine whether there is blood which is an indication that the needle has penetrated a vein or artery and should be reimplanted. Assuming the needle is correctly implanted and that a sufficient amount of anesthetic has been injected to partially anesthetize the localized area, the foot switch is actuated to raise the flow rate to complete the anesthetizing of the tissue of the patient.

When the procedure is completed or when a replacement vial V is required, the hydraulic syringe is disassembled to the point shown in FIG. 7B at which time the compressed resilient member 55 will force the vial V rearwardly from the needle so that it may be easily removed from the forward portion 51 of the syringe. Also, the actuating piston 59 is driven back to its original position (to the right as viewed in FIGS. 7A-D) by appropriate actuation of the foot switch 90.

Figure 9A:
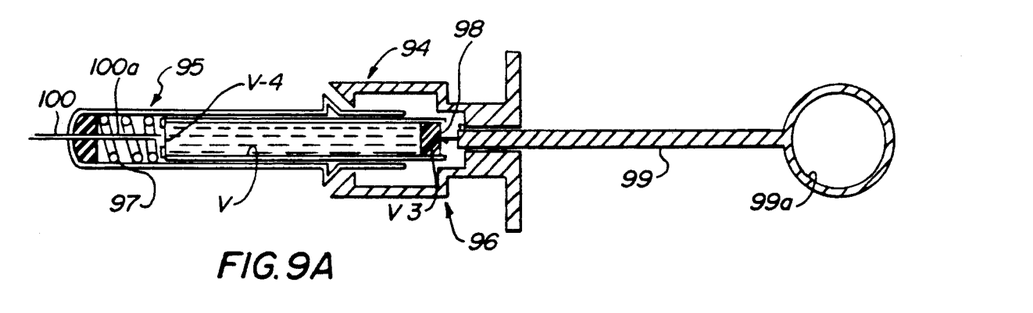
FIG. 9A is a view in horozontal longitudinal section and exploded to show the three sections of a conventional aspirating hypodermic syringe embodying a feature of the present invention.
Figure 9B:
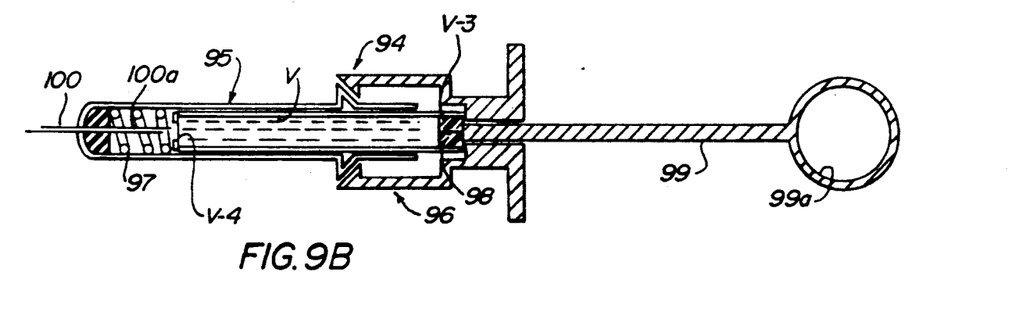
FIG. 9B is a view in longitudinal section corresponding to FIG. 9A and showing the hypodermic syringe partly assembled to engage the driving member with the piston in the anesthetic vial.
Figure 9C:
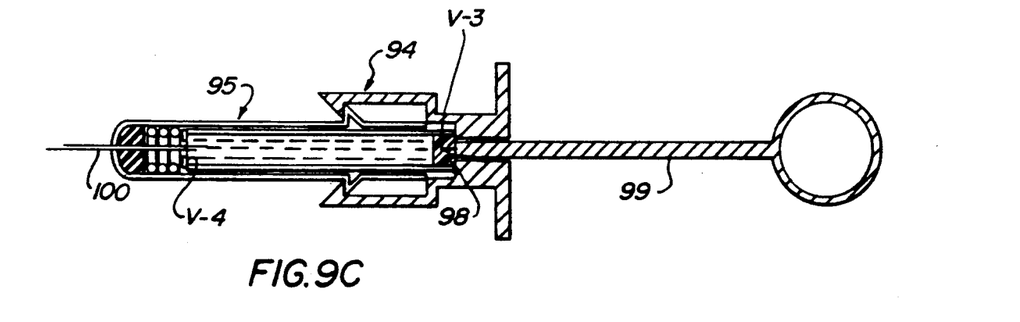
FIG. 9C is a view corresponding to FIG. 9A in which the hypodermic syringe has been completely assembled.
Figure 9D:
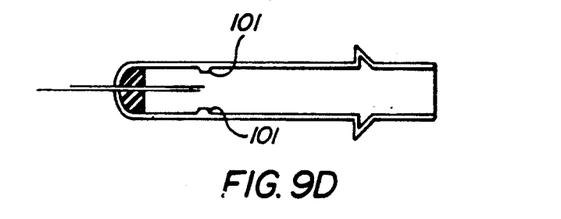
FIG. 9D is a view in longitudinal section of the front portion of the hypodermic syringe assembly of FIGS. 9A-9C showing another embodiment of the invention.

Referring to FIGS. 9A-C a feature of the invention is illustrated as embodied in a conventional aspirating hypodermic syringe 94 comprising a forward needle carrying portion 95, an anesthetic vial V and a rearward hand actuated portion 96. The vial V is identical to that described in connection with FIGS. 7A-F and its part are identified by identical reference numbers. A yieldable resistance in the form of a coil spring 97 is seated in the forward inner end of the forward portion 95 in a manner corresponding to the resilient sleeve 55 of FIGS. 7A-D. As best seen in FIG. 9B, with the vial V inserted into the forward portion 95 and the rearward actuating portion 96 partially but not fully engaged with the forward portion, a barb 98 on the forward end of a thumb actuated plunger 99 will pierce and become coupled in push-pull engagement with the rubber piston V-3 of the vial V. The yieldable resistance of the resilient spring 97 is sufficient to enable the barb 98 to pierce and couple with the piston V-3. When the syringe is fully assembled as shown in FIG. 9C with the front and back portions clamped together, the spring 97 is compressed, having allowed the sharpened inner end 100a of the needle 100 to pierce the forward membrane V-4 in the vial V. From this point the syringe is operated in a conventional manner, with the operator's thumb in the thumb ring 99a of the plunger 99 to perform both injecting and aspirating functions. When the operation is completed or the vial emptied, whichever occurs first, the syringe is disassembled, at which time the compressed spring 97 will force the vial V outward free of the needle 100. The function of the spring 97, therefore, is to ensure that the coupling barb 98 engages with the piston V-3 of the vial 3 before injection of anesthetic through the needle. Because in this embodiment and in the case of most hand operated syringes the length of the vial V exceeds the length of the forward portion 90 of the syringe it is possible for the operator to manually force the vial inward to couple the hollow needle with the anesthetic within the vial before the syringe is assembled. When this has been done it is normally possible to operate the syringe to inject anesthetic into the patient without the barb 93 actually penetrating and coupling to the piston V-3 thus making aspiration impossible and exposing the patient to the possibility of injury due to injection of anesthetic directly into a vein. The present invention precludes this possibility because the spring 97 will force the vial outward away from the needle until such time as the barb 93 is properly coupled to the piston V-3.

The following description is applicable to the embodiments of the invention shown in both FIGS. 7A-F and FIGS. 9A-D. Tests on conventional anesthetic vials show that typical forces for causing the rearward portion 53a or 100a of the double ended needles 53 or 100 to penetrate the piercable membrane V-4 of the vial V are approximately 4 to 5 pounds; forces for driving the piston V-3 in the cylindrical body portion of the vial to expel liquid are approximately 4 to 5 pounds; and forces for causing the barbs 63 or 98 to pierce and engage the piston V-3 in push-pull driving relationship are approximately 5 to 6 pounds. Thus it is possible for a dentist to assemble an aspirating hypodermic syringe with the hollow needle entering the anesthetic reservoir in the vial and with the barb only pushing the piston without establishing a pulling coupling which is essential for the aspiration test. In the event the forward end of the needle 53 or 100 has come to rest in a vein, no blood will show in the vial even though the dentist faithfully follows the age-old procedure of drawing back on the decoupled actuator.

In the embodiment of the invention shown in FIGS. 7 and 9 the yieldable resistance to the movement of the vial V for seating the barb is provided by the resilient rubber sleeve 55 or the spring 97. In the embodiment of FIG. 9D the yieldable resistance is provided by yieldable barriers 101 disposed with the barrel of the syringe. The impedance of the barriers is such that they resist the insertion of the vial to the extent necessary to enable the barb to penetrate and couple to the piston V-3. The barriers 101 are not, however, capable of forcing the vial V in reverse motion away from the needle 94, that is to say, they only yield radially. It is possible, therefore, for an operator to force the vial into its forward position beyond the yieldable barriers prematurely, thereby losing the automatic coupling feature. A resilient resistence with axial thrust is therefore preferred, particularly in cases in which the vial is longer than the forward portion into which it is inserted. It will be understood that the barriers 101 can also be formed in the barrel of the rearward or actuating portion of the syringe, or if desired the yieldable resistance to vial movement can be provided by a friction sleeve fitted over the inner end of the needle to slide thereon with resistance sufficient to insure coupling of the barb to the piston.

While the invention has been described having reference to preferred embodiments it will be understood that it can take other forms and arrangements. For example, the controls for the drive means can take the form of low voltage electrical switches on the handpiece. In general, however, it is preferred that the handpiece be kept light and free of bulk to afford the operator maximum tactile sensation for needle placement and to free the fingers for stabilization of the needle. Also, it will be understood that the present invention can be used for other dental or medical procedures such, for example, as injecting and aspirating medicaments from opened root canals, applying etching acids to precise locations on teeth, injecting and aspirating materials into and from gingival troughs, and injecting flowable cements into teeth. In such cases, different vials and needle configurations will, of course, be required. The invention should not, therefore, be regarded as limited except as defined in the following claims.

What is claimed is:

1. Apparatus for the injection of anesthetics including a hollow hypodermic needle, a handle assembly for carrying the needle, and a single source of liquid anesthetic, the apparatus comprising:
   pump means having a positive duty cycle to expel liquid anesthetic from the needle tip,
   programmed discharge flow rate control means associated with the positive duty cycle to selectively expel liquid anesthetic at a first rate not to exceed 0.25 to 1.0 cc. per minute and at a second rate of greater than approximately 2.0 cc. per minute,
   and control means to select between the first and second flow rates, whereby the first flow rate can be established during implantation of the needle in the tissue to establish a small positive low flow rate during penetration, and the second flow rate can be established after implantation.

2. Apparatus as set forth in claim 1, said pump means being remote from the handle assembly and connected thereto by a flexible conduit.

3. Apparatus as set forth in claim 1 in which the second injection rate is between 2 and 4 cc. per minute.

4. Apparatus as set forth in claim 1 including means to interpose a negative duty cycle to aspirate after a predetermined amount of liquid anesthetic has been expelled from the needle tip whereby liquid anesthetic can be expelled from the needle tip at a rate not to exceed 0.25 to 1.0 cc. per minute as the needle is advanced into the tissue toward its ultimate resting place to anesthetize both the route of needle penetration and the ultimate site of subsequent anesthetization prior to expelling the anesthetic at the second rate.

5. Apparatus as set forth in claim 2 in which the second rate is on the order of 2 to 4 cc. per minute.

6. Apparatus as set forth in claim 4 including means for controlling the rate and duty cycle from a point remote from the handle assembly.

7. Apparatus as set forth in claim 6 including foot controlled switch means for activating and controlling said pump means.

* * * * *